United States Patent [19]

Rheinberger et al.

[11] Patent Number: 5,360,340

[45] Date of Patent: Nov. 1, 1994

[54] PROCESS FOR PRODUCING DENTAL RESTORATIONS AND A POSITIVE WORKING MODEL FOR IMPLEMENTING THE PROCESS

[76] Inventors: Volker Rheinberger, Floraweg 3, FL-9490, Vaduz, Liechtenstein; Viktor Moldaschl, Dorfstr. 8, CH-9472 Grabs, Switzerland

[21] Appl. No.: 626,048

[22] Filed: Dec. 12, 1990

[30] Foreign Application Priority Data

Dec. 16, 1989 [DE] Germany .............................. 3941663

[51] Int. Cl.⁵ ........................ A61C 11/00; A61C 5/08; A61C 5/10
[52] U.S. Cl. ................ 433/213; 433/222.1; 433/223
[58] Field of Search .................. 433/213, 215, 222.1, 433/218, 223

[56] References Cited

U.S. PATENT DOCUMENTS

| | | |
|---|---|---|
| 1,379,689 | 5/1921 | House . |
| 3,748,741 | 7/1973 | Yerkes . |
| 4,207,678 | 6/1980 | Jeannette . |
| 4,226,593 | 10/1980 | Cohen et al. .......................... 433/217 |
| 4,529,384 | 7/1985 | Severy ................... 433/213 |
| 4,721,464 | 1/1988 | Roden et al. . |
| 4,850,871 | 7/1989 | Bryan ................... 433/213 |
| 4,902,232 | 2/1990 | Neustadter .......................... 434/263 |
| 5,127,835 | 7/1992 | Yamaguchi et al. .............. 433/222.1 |

FOREIGN PATENT DOCUMENTS

| | | |
|---|---|---|
| 38186/85 | 8/1985 | Australia . |
| 47873 | 9/1985 | Austria . |
| 22655 | 1/1981 | European Pat. Off. . |
| 30850 | 6/1981 | European Pat. Off. . |
| 231773 | 8/1987 | European Pat. Off. . |
| 234945 | 9/1987 | European Pat. Off. . |
| 374446 | 6/1990 | European Pat. Off. . |

*Primary Examiner*—Paul J. Hirsch
*Assistant Examiner*—Cindy A. Cherichetti
*Attorney, Agent, or Firm*—Cushman, Darby & Cushman

[57] ABSTRACT

Process for producing dental restorations which are exactly matched in shape and in color, especially crowns, and for a positive working modal that can be used for this purpose.

8 Claims, No Drawings

PROCESS FOR PRODUCING DENTAL RESTORATIONS AND A POSITIVE WORKING MODEL FOR IMPLEMENTING THE PROCESS

The invention relates to a process for producing dental restorations from plastic materials or ceramics with exactly matching coloring and to a positive working model suitable for implementing this process. The invention relates in particular to a process for producing crowns from a transparent material such as plastic materials or ceramics and to a dental stump suitable as working model for implementing this process.

It is known to produce dental restorations, especially veneer crowns, from plastic material or ceramics. These dental restorations must be colored to resemble as closely as possible the appearance of the natural teeth. To this end they are painted before polymerisation (plastic material) or firing (ceramics).

This technique is particularly applied with the poured or pressed ceramics, as described in EP-A-231 773, EP-A-30 850 and EP-A-22 665.

With the process according to EP-A 22 655, which is on the market under the name "Dicor", a castable glass ceramic is used, the cast microstructures of which refract and reflect the light in various ways resembling the light diffusion effect of the natural teeth. Heat treatment then gives the dental restoration its final strength and optical quality. To give color, the dental restorations (crowns) are painted with ceramic colors, which are then fired.

These types of dental restorations are produced as follows: the dentist grinds one or more teeth which are to be fitted with dental restorations (crowns). The dentist supplies the dental laboratory with an impression of the remainder of the tooth as well as details on the color of the dental restoration to be produced. The information on the color of the dental restoration is based on commercial color keys, which the dentist has at his disposal.

The dental prosthetist then produces from the impression of the remainder of the tooth a positive plaster working model corresponding to this remainder of the tooth which corresponds spatially to the mouth situation.

With the aid of this plaster model, dental restorations, such as e.g. crowns are produced using known processes according to the above-mentioned prior art. These dental restorations are usually transparent and must be painted so that their color conforms to the mouth environment.

A process for coloring fireable porcelain dental restorations is known from AT 0 047 873. This process allows dental restorations to be individually colored by the dentist himself who applies coloring solutions of various color pigments. After at least a part of the porcelain dental restoration has been coated with a film of such a coloring solution, the film is allowed to harden before a subsequent film is applied. After the predetermined number of films has been applied, the dental restoration is heated, the carrier liquid evaporates and the pigment fuses with the dental restoration and imparts to it a permanent coloring.

The greater or lesser degree of transparency of the dental restorations produced in the above-described manner has the disadvantage that it becomes very difficult for the dental prosthetist to obtain the right coloring solely on the basis of the color determined for the dental restoration, because the ultimately visible color of the tooth is the result of a mix of the chosen color of the dental restoration and of the color of the base, i.e. of the filed remainder of the tooth. Consequently, if the positive plaster working model produced by the dental prosthetist is of a different color from the dental stump remaining in the mouth of the patient—which is usually the case—the resulting mix of colors, i.e. the color that is seen, is likewise different. This means, for example, that if a dental prosthetist has modelled a dental restoration made from plastic material or ceramics on a very light plaster model in the color given by the dentist for the same, when this dental restoration is put on or into a very dark remainder of a tooth, the resulting mix of colors does not conform. This is an unsatisfactory result and does not fulfil the cosmetic requirements.

It has now been found that this disadvantage can be successfully overcome by also determining the color of the remainder of the tooth that remains according to a color key and producing a positive working model in the color thus determined.

Consequently, the aim of the invention is to make available a process for producing dental restorations from plastic material or ceramics with exactly matching coloring, with which it is possible to achieve greater precision in coloring than before and better agreement between the prepared dental restorations and the neighbouring teeth when introduced into the mouth. A further aim of the invention is to create a faithful positive working model which is suitable for implementing this process and therefore for producing a dental restoration from plastic material or ceramics, particularly a spatially matching positive working model that approaches the color of the filed remainder of the tooth so closely that its use enables dental restorations from plastic materials or ceramics to be simply produced with exactly matching coloring.

A process is proposed to achieve this aim.

Furthermore, a positive working model suitable for implementing this process is proposed, that has the same shape as the filed remainder of the tooth and that, with the aid of a color key, has been colored in a color corresponding to the remainder of the tooth, so that by combining the color of the positive working model with the color of the dental restoration the resulting mix of colors is the same as by combining the remainder of the tooth with the dental restoration.

To implement the process of the invention according to the first alternative, firstly a dental restoration blank, e.g. a dental crown, is made in a known manner per se. The preparation of ceramic dental crowns is prior art and is, for example, described in the publications cited above. Subsequently a hardenable material, preferably a hardenable plastic material, is placed in the cavity of the blank in order to obtain the positive working model. In addition to plastic materials, hardenable materials which come into consideration are plaster, investment compounds, ceramics, composites, cements and also elastomeric compounds usually used for casting. They can be hot-, cold- or light-hardening or harden according to other mechanisms. A precondition of the application according to the invention is that these compounds can be colored according to the color of dental stumps. These compounds preferably have a low shrinkage level after hardening.

Of course it is also possible, according to the second alternative, to produce a model from plaster or from another modelling material corresponding to the color of the dental stumps and to use it further as a positive working model.

The dentist selects the color of the dental stump or of the remainder of the denture e.g. with the aid of a known color key. If several teeth are filed, the colors of these stumps can vary, so that the dentist has to select several colors. This information is passed on to the dental prosthetist who, e.g. selects the plastic material in the corresponding color from an existing selection of variously colored plastic materials and subsequently produces the positive working model with it. However, on the basis of this information, the tooth stump can also be colored or painted. It is further possible to color the modelling material according to the color of the remainder of the denture.

Then follows in a final stage, which is common to both variants, the coloring of the dental restoration blank by painting and characterising according to the color details from the dentist. The combination of the two colors previously established with a color key for the dental restoration (e.g. for the crown) and for the working model (tooth stump), makes it much easier to produce the dental restoration and a cosmetically satisfactory result quickly and surely follows.

The following example illustrates the invention:

EXAMPLE

According to EP-A-231 773 and the first alternative of the process, in the first stage a blank of a dental restoration (crown) was made from ceramics: for this the dental prosthetist modelled a crown from a combustible material, preferably from wax, on a normal plaster working model cast from the dental impression. This crown of combustible material was embedded according to known techniques in a hardenable investment compound and the combustible material was removed by heating, a cavity resulting in the investment compound. Applying the measures described in EP-A-231 773 for producing a porcelain dental crown, a ceramics compound which was composed of the following was placed in this cavity:

| | |
|---|---|
| $SiO_2$ | 63% |
| $Al_2O_3$ | 17.7% |
| CaO | 1.5% |
| MgO | 0.05% |
| $Na_2O$ | 4.6% |
| $K_2O$ | 11.2% |
| $Ce_2O_3$ | 0.45% |
| BaO | 0.7% |
| $B_2O_3$ | 0.6% |
| $TiO_2$ | 0.2% |

The thus-obtained porcelain crown was fired in an oven at approximately 1200° C. After firing, the muffle mould was cooled and the crown debedded. It has a certain translucence, i.e. it is transparent.

To produce the positive working model in the second stage the dental prosthetist selected the color (e.g. no. 20) from an existing selection of various-colored tooth-like light-hardening plastic materials according to the information given by the dentist. The selection contains 7 colors according to the Biochromatik color ring from Ivoclar/Vivadent. When the color number is given, the color is clearly fixed. The light-hardening plastics material corresponds to the "Heliosit" light-hardening filling material from Vivadent with the color code 20. This is a light-hardening, micro-filled composite according to DE-PS 24 03 211. The cavity of the crown was brushed in with a commercial insulant and the light-hardening plastics material introduced into the cavity. A stump pin was pressed into the compound. This is preferably a small transparent plastics material tube. After the light-hardening plastics material has been thoroughly hardened with a commercial polymerisation lamp, the crown can be held with the aid of the stump pin.

In the final process stage, the dental prosthetist completed the crown by painting it according to the dentist's color details for the crown, using the individual dental stump. However, it can be equally well completed by veneering with ceramics or plastics material. In either case, coloring takes place quickly and reliably, because the individual positive working model in the color of the dental stump of the patient creates the right condition for speedier and optimised success. This applies not only to more transparent but also more opaque crowns, because by filling the cavity of the crown with the corresponding stump material, a color change naturally occurs even with more opaque crowns, resulting in a mixed color.

In contrast to the previous process, where the agreement of the crown or dental restoration and the remainder of the patient's denture was left to chance and the skill of the dental prosthetist, by producing the faithful positive working model of the invention, the prosthetist can simulate the mouth conditions, the positive working model acting not only as a spatial but also as a color basis for the crown. The advantage of the invention is simply achieved by the dental prosthetist's now working according to two color details, i.e. according the color determined for the dental restoration and the color determined for the positive working model, the dentist determining both color details with a color key.

We claim:

1. Process for producing dental crown restorations from ceramics with exactly matching coloring comprising the steps of:
   (i) producing a crown from ceramics, matching the shape of a tooth, in a known manner,
   (ii) producing a positive working model which matches the shape and color of a ground remainder of the tooth, wherein the color of said positive working model is selected from a group of different-colored light-hardening plastic materials, and
   (iii) coloring the crown for the dental restoration based on a color chosen with a color key and using the obtained positive working model
   wherein said color of said positive working model exactly matches said color of said ground remainder of the tooth.

2. A process for producing dental crown restorations from ceramics with exactly matching coloring comprising the steps of:
   (i) producing a crown matching the shape of a tooth in a known manner,
   (ii) producing a positive working model corresponding to a color selected from an existing selection of various-colored tooth-like light-hardening plastic materials which color exactly corresponds to the color of the remainder of the tooth, and
   (iii) coloring the crown for the dental restoration based on a color chosen with a color key and using the obtained positive working model.

3. A process for producing dental crown restorations from ceramics with exactly matching coloring comprising the steps of:

(i) producing a crown matching the shape of a tooth in a known manner,
(ii) producing a positive working model corresponding to a color selected from an existing selection of various-colored tooth-like light-hardening plastic materials which color exactly corresponds to the color of the remainder of the tooth, and
(iii) coloring the crown for the dental restoration based on a color chosen with a color key and using the obtained positive working model, in which process the ceramics are free of $P_2O_5$.

4. A process for producing dental crown restorations from ceramics with exactly matching coloring comprising the steps of:
(i) producing a crown matching the shape of a tooth in a known manner,
(ii) producing a positive working model corresponding to a color selected from an existing selection of various-colored tooth-like light-hardening plastic materials which color exactly corresponds to the color of the remainder of the tooth, and
(iii) coloring the crown for the dental restoration based on a color chosen with a color key and using the obtained positive working model, in which process the ceramic is composed of the following compounds:

| | |
|---|---|
| $SiO_2$ | 63% |
| $Al_2O_3$ | 17.7% |
| CaO | 1.5% |
| MgO | 0.05% |
| $Na_2O$ | 4.6% |
| $K_2O$ | 11.2% |
| $Ce_2O_3$ | 0.45% |
| BaO | 0.7% |
| $B_2O_3$ | 0.6% |
| $TiO_2$ | 0.2%. |

5. A positive working model consisting of a light-hardening plastic material and exactly matching the shape and color of a ground remainder of a tooth in the mouth.

6. Process for producing dental crown restorations from ceramics with exactly matching coloring comprising the steps of:
(i) producing a crown from ceramics, matching the shape of a tooth, in a known manner,
(ii) producing a positive working model which matches the shape and color of a ground remainder of the tooth, wherein the color of said positive working model is selected from a group of different-colored, light-hardening plastic materials, and
(iii) coloring the crown for the dental restoration based on a color chosen with a color key and using the obtained positive working model wherein said color of said positive working model exactly matches said color of said ground remainder of the tooth and wherein the ceramics are free of $P_2O_5$.

7. Process for producing dental crown restorations from ceramics with exactly matching coloring comprising the steps of:
(i) producing a crown from ceramics, matching the shape of a tooth, in a known manner,
(ii) producing a positive working model which matches the shape and color of a ground remainder of the tooth, wherein the color of said positive working model is selected from a group of different-colored, light-hardening plastic materials, and
(iii) coloring the crown for the dental restoration based on a color chosen with a color key and using the obtained positive working model wherein said color of said positive working model exactly matches said color of said ground remainder of the tooth and wherein the ceramic, which does not contain $P_2O_5$, comprises the following elements: $SiO_2$, $Al_2O_3$, CaO, MgO, $Na_2O$, $K_2O$, $Ce_2O_3$, BaO, $B_2O_3$, and $TiO_2$.

8. The process of claim 7 wherein the ceramic comprises 63% $SiO_2$, 17.7% $Al_2O_3$, 1.5% CaO, 0.05% MgO, 4.6% $Na_2O$, 11.2% $K_2O$, 0.45% $Ce_2O_3$, 0.7% BaO, 0.6% $B_2O_3$, and 0.2% $TiO_2$.

* * * * *